United States Patent [19]

Hanson

[11] Patent Number: 5,399,352
[45] Date of Patent: Mar. 21, 1995

[54] DEVICE FOR LOCAL DRUG DELIVERY AND METHODS FOR USING THE SAME

[75] Inventor: Stephen R. Hanson, Stone Mountain, Ga.

[73] Assignee: Emory University, Atlanta, Ga.

[21] Appl. No.: 46,622

[22] Filed: Apr. 14, 1993

[51] Int. Cl.⁶ .............................. A61F 2/04; A61F 2/06
[52] U.S. Cl. ............................................ 424/423; 623/1; 623/12
[58] Field of Search ...................... 424/423; 623/1, 12

[56] References Cited

U.S. PATENT DOCUMENTS

| | | | |
|---|---|---|---|
| 3,797,485 | 3/1974 | Urquhart | 128/213 |
| 4,687,482 | 8/1987 | Hanson | 623/1 |
| 5,192,310 | 3/1993 | Henveck et al. | 623/1 |

OTHER PUBLICATIONS

Hanson et al., *Arteriosclerosis* 5:595–603 (1985).
Kelly et al., *Blood* 77:1006–1012 (1991).
Hanson et al., *Proc. Natl. Acad. Sci. USA* 85:3184–3188 (1988).

*Primary Examiner*—G. S. Kishore
*Assistant Examiner*—Carlos Azpuru
*Attorney, Agent, or Firm*—Needle & Rosenberg

[57] ABSTRACT

A device for the local delivery of a substance into a natural tissue conduit in the mammalian body, having a first element capable of contacting the lumen of the conduit and a second element which overlays first element, a reservoir being formed between the first element and the second element, the interior of the reservoir being capable of fluid communication with the conduit such that a substance placed in the reservoir is delivered into the conduit. Also provided are methods of locally delivering a substance into a natural tissue conduit in the mammalian body utilizing the device of the present invention.

26 Claims, 3 Drawing Sheets

DEVICE FOR LOCAL DRUG DELIVERY AND METHODS FOR USING THE SAME

ACKNOWLEDGEMENTS

This invention was made with government support under Grant Number HL 31469 awarded by the National Institutes of Health. The government has certain rights in the invention.

FIELD OF THE INVENTION

This invention relates to a device for the local delivery of a substance into a natural tissue conduit, e.g., a blood vessel, and to methods of therapy utilizing the device.

BACKGROUND OF THE INVENTION

One of the most complex and difficult problems that has plagued the medical profession and pharmaceutical industry for decades is the problem of achieving a therapeutic concentration of a drug locally at a target site within the body without producing unwanted systemic side effects. Parenteral or oral therapy of substances directed at treating disease in a particular internal organ must often be given in amounts dependant upon achieving critical systemic blood levels that can produce devastating side effects at other areas in the body. A prime example of a situation where local therapy is needed with drugs that also produce unwanted systemic side effects is the prevention of complications following the placement of a cardiovascular prosthetic device such as a prosthetic vascular graft or a patch used to repair a damaged vessel.

Graft failure is often associated with the inherent thrombogenicity of the blood contacting surface of the prosthetic device and with the body's own repair mechanisms which can lead to progressive stenotic occlusion due to neointimal fibrosis and hyperplasia. Systemic therapy aimed at preventing coagulation and thrombosis locally at the graft site is often complicated by bleeding at other sites. Likewise, systemic treatment with growth mediators or chemotherapeutic agents can produce a hyperplastic or hypoplastic response in tissue not specifically targeted. Similarly, administration of vasodilators can produce systemic hypotension.

There have been many attempts to render vascular grafts less thrombogenic, e.g., by coating the luminal surface of the graft with non-thrombogenic polymers (U.S. Pat. No. 4,687,482), cells (U.S. Pat. No. 5,037,378) or with anticoagulant drugs in a polymer coating (PCT Application WO 91/12279). Although these attempts have improved the success associated with graft placement, complications with clotting, thrombosis, and restenosis, especially that seen due to fibroplasia and smooth muscle proliferation, still abound. Therefore, there exists a need in the art for a means and a method of providing local therapy which can sustain high local concentrations of therapeutic drugs at the site of vessel repair thereby preventing complications associated with placement of the prosthetic graft without producing unwanted systemic side effects.

SUMMARY OF THE INVENTION

The present invention satisfies that need by providing a device for local delivery of a drug to the graft site comprised of a vascular graft with a porous portion and a reservoir for the drug attached to the external surface of the graft and overlying the porous portion such that the interior of the reservoir is in fluid communication with the luminal, blood flow contacting surface of the vascular graft via the porous portion wherein a drug placed in the reservoir is delivered to the luminal surface of the graft. The present invention also provides a vascular patch constructed in like fashion. One embodiment of the present invention, provides a tubing attached to and in communication with the reservoir such that the reservoir can be refilled with drug or the drug changed as therapeutic needs change. Another embodiment of the invention further comprises a pump connected to the tubing to deliver drug to the reservoir and to maintain a desired pressure within the reservoir. The present invention also provides methods for treating or preventing, including but not limited to, coagulation, thrombus formation, fibrosis and restenosis associated with vascular prosthetic devices.

There also exists a need to provide effective local therapy for treatment of cancer and other diseases in many areas of the body such that the chemotherapy can be localized to targeted tissues, thereby preventing unwanted systemic side effects from systemic administration. The present invention satisfies that need by providing a means to locally deliver a substance into any natural tissue conduit of the mammalian body and thereby provide localized therapy to targeted tissues. Alternate embodiments of the invention can be utilized to provide local drug delivery to any conduit, including but not limited to, lymphatic vessels, bile ducts, ureters, the intestinal tract, and the respiratory tree. For example, a transitional cell carcinoma of the bladder can be effectively treated with chemotherapeutic agents by insertion of the device of the present invention into a ureter and administering the appropriate drug.

DETAILED DESCRIPTION OF THE INVENTION

Figure 1:
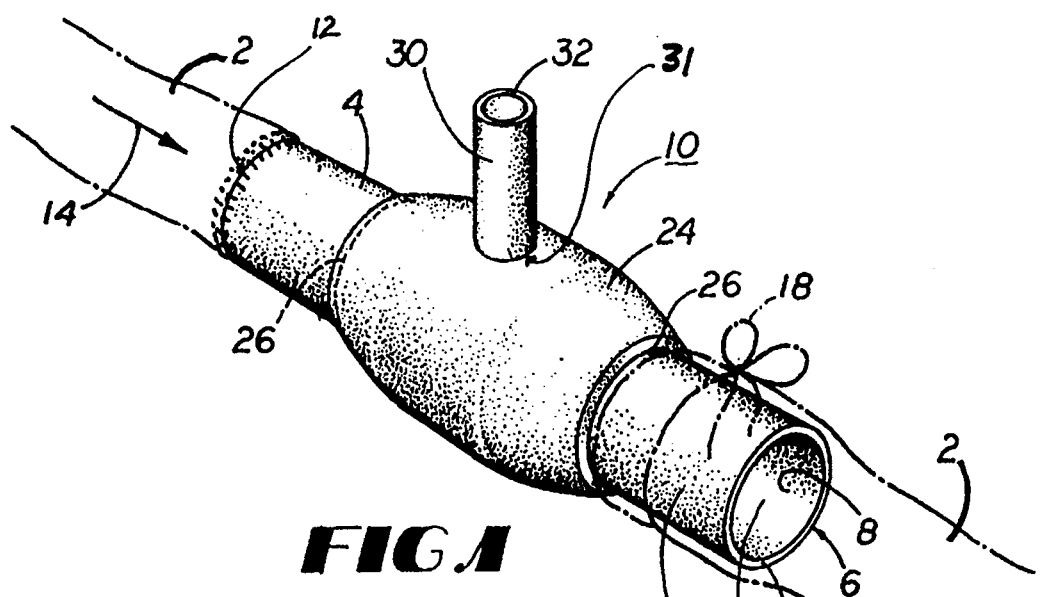
FIG. 1 is a perspective view of the first embodiment of the present invention showing the local drug delivery device attached to a natural tissue conduit, e.g., a blood vessel, proximally by anastomosis and distally by cannulation.

The present invention may be understood more readily by reference to the following detailed description of specific embodiments and the Examples and Figures included therein.

As used in the claims, "a" can mean one or more.

The present invention provides a device for the local delivery of a substance into a natural tissue conduit in the mammalian body, comprising: a first element comprised of a biocompatible material which can be affixed to the conduit having a first surface, an opposite second surface, and an intermediate porous portion which communicates the second surface with the first surface, wherein the first surface of the porous portion is capable of contacting the lumen of the conduit; and a second element comprised of a substantially non-porous biocompatible material which overlays the second surface of the first element, a reservoir being formed between the first element and the second element, the interior of the reservoir being capable of fluid communication with the conduit via the porous portion such that a substance placed in the reservoir is delivered into the conduit.

The phrase "natural tissue conduit" as used herein means any area of the mammalian body which functions to transport substances and includes, but is not limited to, e.g.; blood vessels of the cardiovascular system (arteries and veins), the lymphatic system, the intestinal tract (esophagus, stomach, the small and large intestines, and colon), the portal-caval system of the liver, the gall bladder and bile duct, the urinary system (ureters, bladder and urethra), the respiratory system (trachea, bronchi, and bronchioles), and ducts and ductules connecting endocrine organs to other areas of the body. The device of the present invention can be used in any mammal or in any animal in which natural tissue conduits are found.

The present invention also provides a device for the local delivery of a substance into a natural tissue conduit in the mammalian body, wherein the first element further comprises an elongated tubular segment having a substantially non-compliant, hollow body portion which is open at both ends wherein the first surface is the luminal surface of the tubular segment, and wherein the tubular segment is capable of being affixed to the natural tissue conduit at both of the ends of the tubular segment. The first element of the device can consist of any tube, porous throughout or porous only through that portion where drug is infused (e.g., porous only at that portion which communicates with the reservoir and the natural tissue conduit). Either end or both ends of the tubular segment can be designed to be inserted intraluminally or anastomosed surgically between segments of any natural tissue conduit.

One embodiment of the present invention comprises the device described above wherein the first element forms a tubular prosthesis with the conduit. In the first embodiment, the conduit can be a blood vessel and the first element a tubular vascular prosthesis as depicted in FIG. 1–FIG. 4.

In the first embodiment of the invention, the tubular vascular prosthesis can be a clinical vascular graft comprised of a porous portion which communicates the reservoir with the lumen of the subject blood vessel. This embodiment can be utilized to provide local drug delivery by utilizing arterial blood flow for prevention or treatment of any disease or condition distal to the site of arterial implantation of the device. Particular examples where the devices of the present invention can be utilized include, but are not limited to, local drug delivery to treat cancer or to maintain perfusion of tissue or organ transplants while the body establishes revascularization of the subject tissue, or as a dialysis access graft. For dialysis access applications, the first element can consist of a suitable synthetic graft material, e.g., GORE-TEX® (which can be repeatedly punctured), in a tapered inside diameter design. The reservoir can be positioned proximal to the dialysis access site on the graft and utilized to deliver drugs which prevent hyperplasia, thrombosis and occlusion at the distal end of the graft.

The devices of the present invention can also function as an improved vascular graft such that the substance or drug placed in the reservoir prevents or treats complications associated with conventional vascular graft placement, including but not limited to platelet deposition, coagulation, thrombosis, neointimal hyperplasia and fibrosis. In particular, the device as described above can be utilized as a peripheral arterial graft, e.g., in a femoral-tibial or femoral-popliteal application to treat peripheral arterial disease of the distal limbs, or as a coronary artery graft. The device can be constructed in a variety of sizes such that the inside diameter of the first element is between about 1 mm and 50 ram, thereby allowing the surgeon to select the appropriate size to accommodate a particular vascular application. Likewise, the porosity (internodal distance) of the porous portion can be varied to affect the rate of drug release.

Alternatively, the first element of the device can comprise a patch which overlies a portion of the conduit. In particular, the present invention provides the device described above wherein the conduit is a blood vessel and the first element is a vascular patch as depicted in the second embodiment in FIG. 5–FIG. 7. As with the tubular segment, the patch can be porous throughout or porous only through that portion where drug is infused. The patch can be constructed from the same materials described herein for the tubular segment, e.g., constructed from any biocompatible materials such as polymers, metals or ceramics.

The first surface of the device of the present invention can further comprise a coating on a portion of the surface in contact with the lumen of the conduit which improves the biocompatibility of the first surface. For example, a portion of the luminal surface of the first element, i.e., the luminal surface of a vascular graft or vascular patch, can be coated with a polymer selected from the group including, but not limited to, fluorocarbon, hydrocarbon, silicone rubber and polyurethane based polymers. As one skilled in the art can appreciate, the luminal surfaces of the first element, depending upon the specific application, can be coated to improve biocompatibility by methods which include, but are not limited to, dip coating, radiation grafting, radiofrequency or glow discharge, polymerization, or other vapor phase thin film coating approaches. (See, e.g., A. S. Hoffman et al., *Radiation Phys. Chem.*, 22:267–283 (1983); A. M. Garfinkle et at., *Trans. Am. Soc. Artificial Intern. Organs*, 30:432–439 (1984); A. S. Hoffman et al., *J. Biomed. Mater. Res.*, 26:357–372 (1992); and Y. S. Yeh et al., *J. Biomed. Mater. Res.*, 22:795–818 (1988)).

The device of the present invention can further comprise a tube, having its first end in communication with the reservoir, and its second end in communication with a remote source of the substance. The device can also comprise a pump connected to the second end of the tube for delivering a substance to the reservoir and for creating pressure within the reservoir which exceeds the intraluminal pressure of the natural tissue conduit. The tubing and pump can be constructed from any biocompatible material, including but not restricted to, silicone rubber, polyurethanes, fluorocarbon polymers, polyethylene, polyvinylchloride or other polymers.

The drug source and/or the pump connected to the tubing can be external or internal, e.g., implanted. One skilled in the art can appreciate the many commercially available infusion pumps which are available that can be connected to the device of the present invention to provide constant controlled rate delivery of a substance to the reservoir. An example of such a pump is the implantable ALZET® osmotic pump marketed by ALZA Corporation, Palo Alto, Calif.. Alternatively, the drug source can be refillable, e.g., an internal implant which is refilled via syringe injection through a skin button, or the drug-source can be a non-refillable reservoir.

As contemplated by the present invention, the substance in the reservoir can be any substance, including any drug, and the device can be used for local delivery of such substances to prevent or treat a variety of disease syndromes or to promote or enhance desired activity within the body. In particular, the present invention provides embodiments of the device described above with a substance implanted in the reservoir. For example, the substance can be an anticoagulant, including but not limited to, heparin, hirudin, hirulog, hirugen, activated and non-activated protein C, synthetic or naturally occurring antagonists of thrombin, and Factor Xa, or other activated or non-activated coagulation protease inhibitors and coagulation factors, e.g., FBI, FIX, FVIII, FV, FVII and tissue factor.

Another embodiment of the present invention provides the device described herein wherein the substance in the reservoir inhibits platelet deposition and thrombus formation or promotes thrombolysis and thrombus dissolution. Examples of such substances include, but are not limited to, plasmin, tissue plasminogen activator (tPA), urokinase (UK), single chain prourokinase (scuPA), streptokinase, prostaglandins, cyclooxygenase inhibitors, phosphodiesterase inhibitors, thromboxane synthetase inhibitors; antagonists of glycoprotein receptors including (GP) Ib, GP IIb/IIIa, antagonists of collagen receptors, and antagonists of platelet thrombin receptors.

In an alternative embodiment, the present invention provides the device described herein wherein the substance in the reservoir affects platelet metabolic function. Examples of such substances include, but are not limited to, prostaglandins, cyclooxygenase inhibitors, phosphodiesterase or thromboxane synthetase inhibitors, inhibitors of calcium transport, or elevators of cyclic adenosine monophosphate (cyclic AMP).

Still another embodiment of the present invention provides the device described herein wherein the substance in the reservoir prevents restenosis of a blood vessel. Examples of such substances include, but are not limited to, a growth factor, a growth factor inhibitor, growth factor receptor antagonist, transcriptional repressor, translational repressor, antisense DNA, antisense RNA, replication inhibitor, inhibitory antibodies, antibodies directed against growth factors or their receptors, bifunctional molecules comprising a growth factor and a cytotoxin, and bifunctional molecules comprising an antibody and a cytotoxin.

The substance in the device of the present invention can also be a vasodilator, such as nitroglycerin, nitroprusside or other nitric oxide liberators. The vasodilator can also include other suitable vasoactive agents such as beta receptor blocking drugs, inhibitors of intra-cellular calcium transport; prostaglandins, thromboxane antagonists, and the like.

The present invention further provides a method of locally delivering a substance into a natural tissue conduit in the mammalian body, comprising the steps of: forming a device comprising a first element comprised of a biocompatible material which can be affixed to the conduit having a first surface, an opposite second surface, and an intermediate porous portion which communicates the second surface with the first surface, wherein the first surface of the porous portion is capable of contacting the lumen of the conduit, and a second element comprised of a substantially non-porous biocompatible material which overlays the second surface of the first element, a reservoir being formed between the first element and the second element, the interior of the reservoir being capable of fluid communication with the conduit via the porous portion such that a substance placed in the reservoir is delivered into the conduit; placing a substance in the reservoir; and affixing the device to the natural tissue conduit such that the first surface of the porous portion contacts the lumen of the conduit and such that the interior of the reservoir is in fluid communication with the conduit via the porous portion of the first element.

The present invention also provides a method of locally delivering a substance into a natural tissue conduit in the mammalian body, comprising affixing to a natural tissue conduit a device comprising a first element comprised of a biocompatible material which can be affixed to the conduit having a first surface, an opposite second surface, and an intermediate porous portion which communicates the second surface with the first surface, wherein the first surface of the porous portion is capable of contacting the lumen of the conduit, and a second element comprised of a substantially non-porous biocompatible material which overlays the second surface of the first element, a reservoir being formed between the first element and the second element, the interior of the reservoir being capable of fluid communication with the conduit via the porous portion such that a substance placed in the reservoir is delivered into the conduit.

The local drug delivery devices of the present invention can be utilized as the device which is affixed to the natural tissue conduit in the methods of local drug delivery described above. The methods of local drug delivery of the present invention can be utilized to deliver any substance into any natural tissue conduit in the mammalian body. The methods described herein are meant to include any substance or drug which can be placed in the reservoir. Certain other embodiments of the invention include methods for locally delivering a substance into a natural tissue conduit in the mammalian body wherein the substances are those substances and drugs previously described herein for preventing or treating restenosis, inhibiting platelet deposition and thrombus formation, promoting thrombolysis, or affecting vascular tone. It is also contemplated that the vasodilators and anticoagulants described herein can be utilized in the methods described above.

Utilizing the methods for predicting downstream concentration of substances (administered by the methods and devices of the present invention) that are taught in the examples, one skilled in the art can determine suitable dosage requirements and treatment regimens for any substance placed in the reservoir of the device. Dosages and regimens will vary, of course, depending upon the tissue targeted for therapy and upon the particular drug utilized. In particular, the substances for preventing or treating restenosis, inhibiting platelet deposition, and thrombus formation, and the vasodilators and anticoagulants described herein can be utilized in the methods for local drug delivery taught herein in amounts determined by the methods taught in the examples and by other optimization procedures known in the art.

One embodiment of the present invention provides a method for locally delivering a substance into a natural tissue conduit wherein the substance inhibits platelet deposition and thrombus formation on a prosthetic cardiovascular device which has been implanted in the cardiovascular system of a subject. The phrase "prosthetic cardiovascular device" includes, but is not limited to, devices such as tubular synthetic grafts, extracorporeal circuits, artificial kidneys, ventricular assist devices, total heart prostheses or oxygenators. As one skilled in the art can appreciate, the method can include, but is not limited to, any of the substances which inhibit platelet deposition and thrombus formation described herein.

Figure 2:
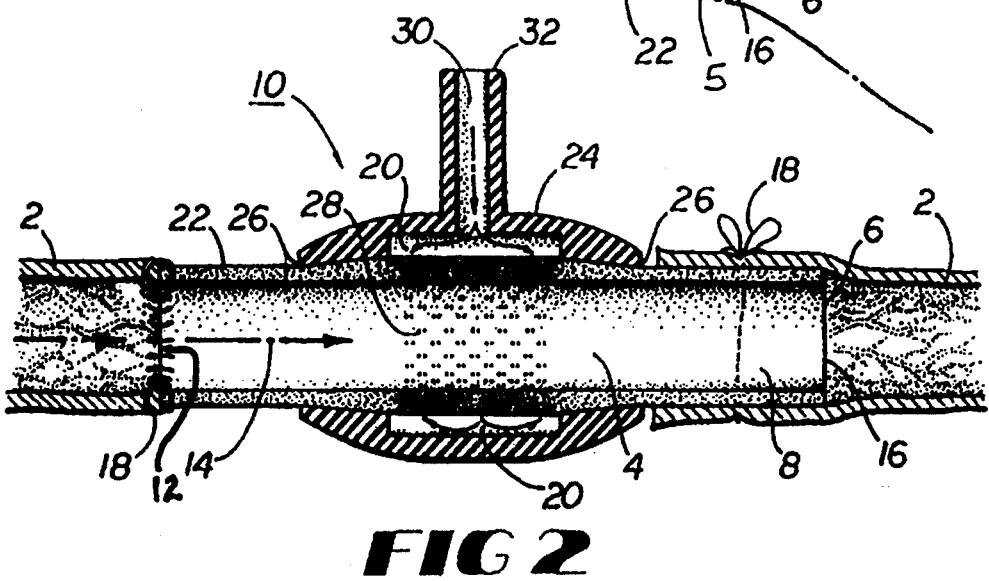
FIG. 2 is a cross-sectional view of the first embodiment of the present invention showing the local drug delivery device attached to a natural tissue conduit.

Referring to FIG. 1 and FIG. 2, depicted is the first embodiment of the present invention wherein the local drug delivery device 10 is affixed to a natural tissue conduit 2 (e.g., an artery). In this example, the first element 4 comprises an elongated tubular segment 5 having a substantially non-compliant, hollow body portion which is open at both ends 6, 12. The first surface 8 is the luminal surface of the tubular segment 5 and is the flow contacting surface for the tissue conduit 2. The tubular segment 5 is capable of being affixed to the natural tissue conduit 2 at both ends 6, 12. In a preferred embodiment, the tubular segment 5 of the first element 4 comprises a porous clinical vascular graft attached to the natural tissue conduit (e.g., an artery) 2 as shown in FIG. 1–FIG. 4.

The first element 4 of the device 10 can be comprised of any biocompatible material, including but not limited to, conventional vascular graft materials such as TEFLON® (polytetrafluoroethylene), DACRON® (polyethylene terephthalate), biocompatible polyesters or other biocompatible polymers. Alternatively, the first element 4 can be comprised of biocompatible metals or ceramics.

In the first embodiment depicted in FIG. 1 and FIG. 2, the device is designed to avoid leakage (e.g., bleeding) at the distal anastomotic site (note the arrow 14 depicting the direction of flow of fluid through the conduit 2). The first element 4 forms a cannula tip 16 at the distal end 6 designed to be inserted into the lumen of the conduit 2 (e.g., an artery). A suture 18 is placed around the circumference of the external surface of the conduit 2 to aid in sealing the distal anastomosis. The proximal end 12 of the tubular segment 5 is sealed by surgical anastomosis of the conduit 2 to the device 10 by suturing the first element 4 via sutures 18 to the conduit 2. In the embodiment depicted by FIG. 3 and FIG. 4, the ends 6, 12, of the first element 4, of the device 10 can be affixed to the conduit 2 by surgical anastomosis of the conduit 2 to the respective ends 6, 12 by sutures 18.

Figure 3:
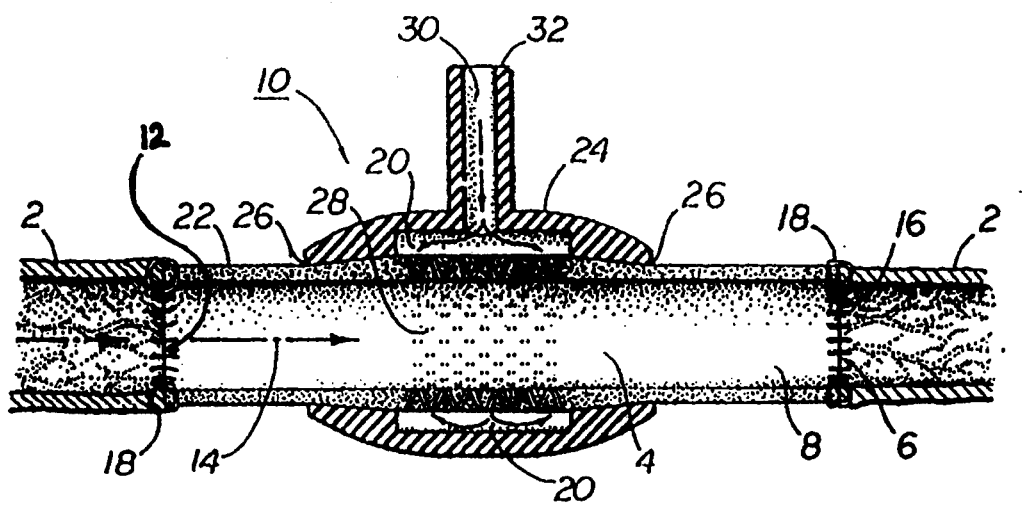
FIG. 3 is a cross-sectional view of the first embodiment of the present invention showing proximal and distal attachments to a natural tissue conduit by surgical anastomosis.
Figure 4:
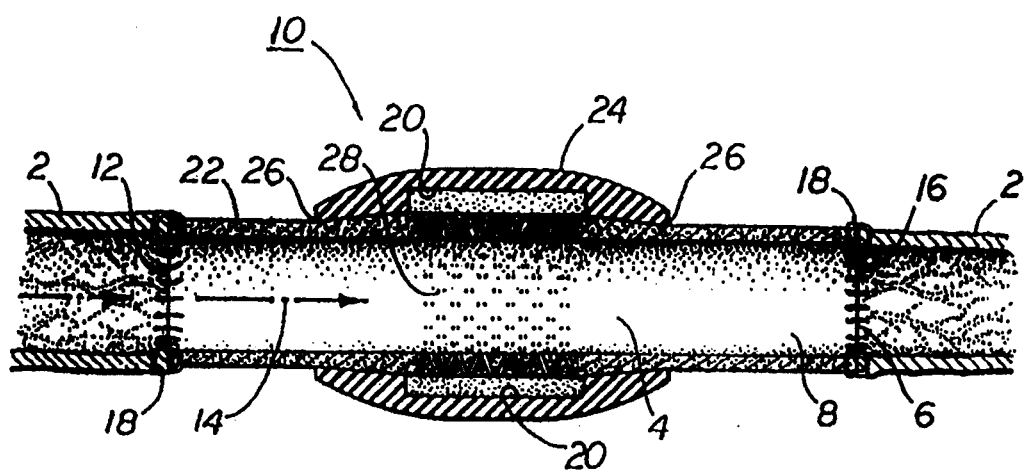
FIG. 4 is a cross-sectional view of the first embodiment of the local drug delivery device attached to a natural tissue conduit.

The reservoir 20 of the device 10 of FIG. 1–FIG. 4 is formed between the second surface 22 of the first element 4 and the second element 24. A liquid tight seal 26 is formed along the edge of the second element 24 where it meets the second (or external) surface 22 of the first element 4. The reservoir 20 communicates with the lumen of the conduit (e.g., an artery) 2 through a porous portion 28 of the first element 4 such that a substance placed in the reservoir 20 is delivered into the lumen of the conduit 2. As depicted in FIG. 1–FIG. 3, the reservoir 20 can be connected to a remote source of the substance (e.g., a drug) via tubing 30 which is in communication at its first end 31 with the reservoir and at its second end 32 with the remote source (not shown) of the substance or drug. Alternatively, the reservoir 20, as depicted in FIG. 4, can be non-refillable and may contain any suitable substance or drug for local delivery through the porous portion 28.

The second element 24 can be constructed from any suitable substantially non-porous biocompatible material, including but not limited to, silicone rubbers, metals, ceramics, polymers such as polyurethane, polyfluorocarbon, polyethylene, polycarbonate, or polyvinyl chloride. Depending upon the choice of materials, the edges of the second element :14 can attached to the first element 4 by appropriate means to form a substantially liquid tight seal 26, thereby forming the reservoir 20 between the first and second elements. A skilled artisan can appreciate the many ways to form the seal for the reservoir 20, e.g., a second element constructed of polymer can be sealed to the first element by polymerizing, casting, injection molding or extruding.

Figure 5:
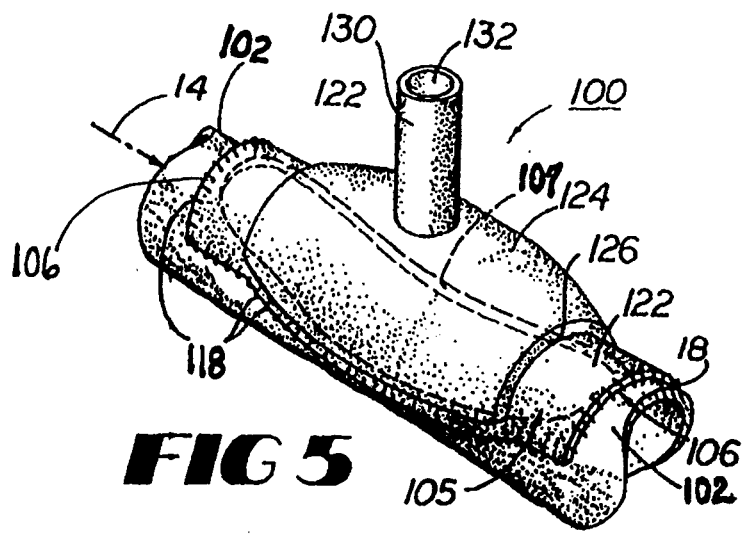
FIG. 5 is a perspective view of the second embodiment of the present invention showing the local drug delivery device forming a patch on a natural tissue conduit, e.g., a blood vessel.
Figure 6:
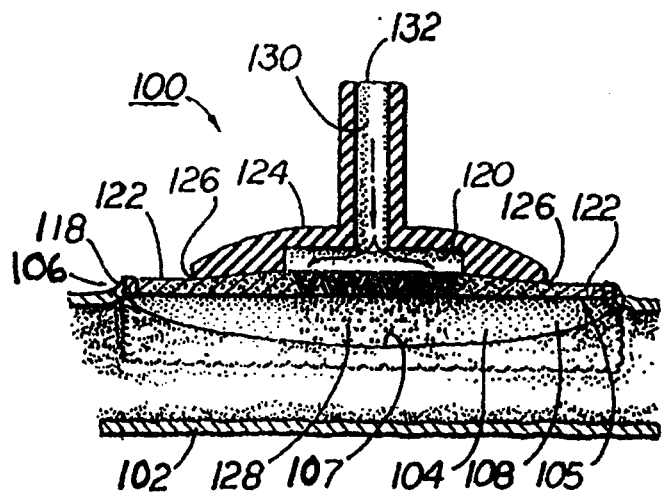
FIG. 6 is a cross-sectional view of the second embodiment of the present invention showing the local drug delivery device forming a patch on a natural tissue conduit.
Figure 7:
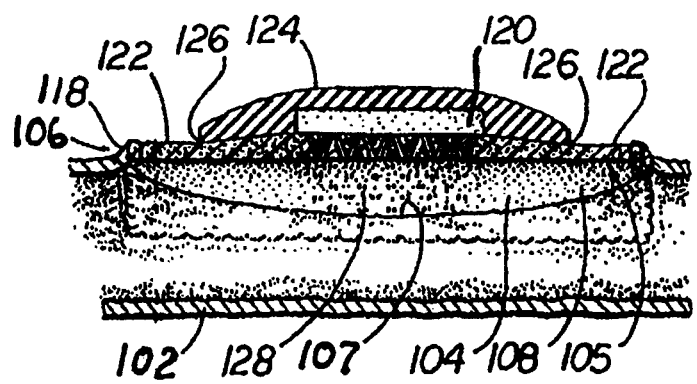
FIG. 7 is a cross-sectional view of the second embodiment of the present invention showing the local drug delivery device attached to a natural tissue conduit.

Referring to FIG.5–FIG. 7, depicted is the second embodiment of the present invention wherein the local drug delivery device 100 forms a patch over a natural tissue conduit (e.g., an artery) 102. The first element 104 comprises a vascular patch which is designed for surgical anastomosis to a man-made aperture 107 in the wall of the conduit (e.g., an artery) 102. The first surface 108 of the first element 104 is the luminal or flow contacting surface. The first element 104 contains a porous portion 128 which allows communication between the lumen of the conduit 102 and the reservoir 120, which is formed between the second surface 122 of the first element 104 and the second element 124. A substantially liquid tight seal 126 is formed at the juncture of the edges of the second element 124 and the second surface 122 of the first element 104. A tube 130 is connected at its first end 131 to the reservoir 120 and is connected to a remote source (not shown) of the substance at its second end 132. The drug delivery device 100 is attached to the conduit 102 by surgical anastomosis of the edges 106 of the first element 104 to the wall of the conduit 102 at the edges of the man-made aperture 107 via sutures 118. Alternatively, the reservoir 120 of the device 100 as depicted in FIG. 7, can be non-refillable. The reservoir can contain any suitable substance or drug for local delivery through the porous portion 128.

The devices and methods of therapy described herein achieve very high drug concentrations locally while minimizing total drug requirements and circulating drug levels, therefore allowing for the efficient use of agents which are available in limited amounts or which could produce side effects. The examples contained herein provide: 1) a theoretical analysis of the convective diffusion problem for the local infusion flow geometry; 2) in vitro studies with measurements of wall drug concentrations distal to infusion sites; 3) results of studies conducted utilizing a baboon ex vivo shunt system and the local delivery device of the present invention to block distal thrombus formation; and 4) in vivo studies with local infusion of basic fibroblast growth factor (FGF) and hirudin (an anticoagulant) at sites of carotid artery angioplasty. These examples document that the local infusion device of the present invention is remarkably efficient, delivers agents uniformly, and can be successfully used to block in vivo thrombus formation and modulate vascular healing.

The examples specifically show that:
1. In typical usage situations drug concentration at the distal vessel wall are about 200 times greater than the average drug concentration (averaged over the entire vessel cross section).
2. Local administration of antithrombotic agents reduces total dose requirements (vs. intravenous therapy) by nearly 3 orders of magnitude for agents having short in vivo half lives, e.g., PPACK antithrombin(D-Phe-Pro-Arg chloromethyl ketone).
3. Following surgical implantation at balloon angioplasty sites, infusion of hirudin markedly inhibits SMC proliferation (by 80%), while infusion of bFGF markedly increases SMC proliferation (to nearly 100%). The blood-contacting surface through which agents are infused remains clean, without evidence of blood element fouling.

The following examples document the reproducibility and efficiency of the methods of therapy and the devices described herein.

EXAMPLES

Throughout this application, various publications are referenced. The disclosures of these publications in their entireties are hereby incorporated by reference into this application in order to more fully describe the state of the art to which this invention pertains.

I. Theoretical analysis. The theoretical problem of predicting downstream wall concentrations of material infused through the wall of a 4 tube having 100 ml/min lumenal blood flow, typical of medium-sized and coronary arteries, has been solved by the present invention. In brief, a supercomputer was used to numerically solve the 2-dimensional Navier-Stokes and species conservation equations using a finite volume element program (Fluent, Inc., Lebanon, NH). The analysis predicts that when the drug-containing buffer is infused through the wall of the device described herein at a low rate (0.05-0.1 ml/min), then the wall concentration of drug at 1-5 cm downstream will be 10-20% of the drug concentration in the infusate, i.e., infused materials are diluted 80-90%, but achieve wall concentrations 200 times greater than would be obtained by infusing drug uniformly over the entire tube cross section. Infused material is confined to a very thin boundary layer (approximately 250 microns thick) along the tube wall. Wall drug concentration is therefore determined by the volume and concentration of drug infused. Since at higher infusion rates (>1 ml/min) it is possible to nearly saturate the distal vessel wall with infusate, we chose in subsequent experimental studies to infuse highly concentrated reagents at a low rate (0.05-0.01 ml/min) to avoid significant buffer dilution of blood at the vessel wall.

II. In vitro studies. One embodiment of the local drug delivery devices of the present invention utilized for continuous administration of agents was constructed as described. In brief, the device consisted of a short length (approximately 2 era) of a standard expanded TEFLON ® vascular graft (GORE-TEX ®, 30 $\mu$internodal distance) having an inner diameter of 4.0 min. The inside diameters for the devices of the invention can range from between about 1-50mm. Likewise, for grafts of this type, the preferred range of internodal distance, a measure of porosity, can range from about 10 $\mu$ to 90 $\mu$.

A silicone rubber cuff-reservoir was placed around the graft for infusion of agents through the graft wall, which, therefor, can enter the flow stream only at the portion of the reservoir overlying the graft interface. To study this system in vitro, Evan's blue dye was infused (0.05-0.1 ml/min) with water flow through the device (30 ml/min) scaled for the viscosity difference between water and blood to simulate 100 ml/min blood flow. Dye entered the lumenal space uniformly, around the entire graft circumference. Dye sampling was performed using collection cuffs placed 1-3 cm downstream. Concentration values, obtained by colorimetric analysis, were within 10% of those predicted theoretically (presumably since the experimental flow conditions were not theoretically perfect). Nonetheless, the excellent agreement between theory and experiment confirmed that these devices function in the intended manner.

Figure 8:
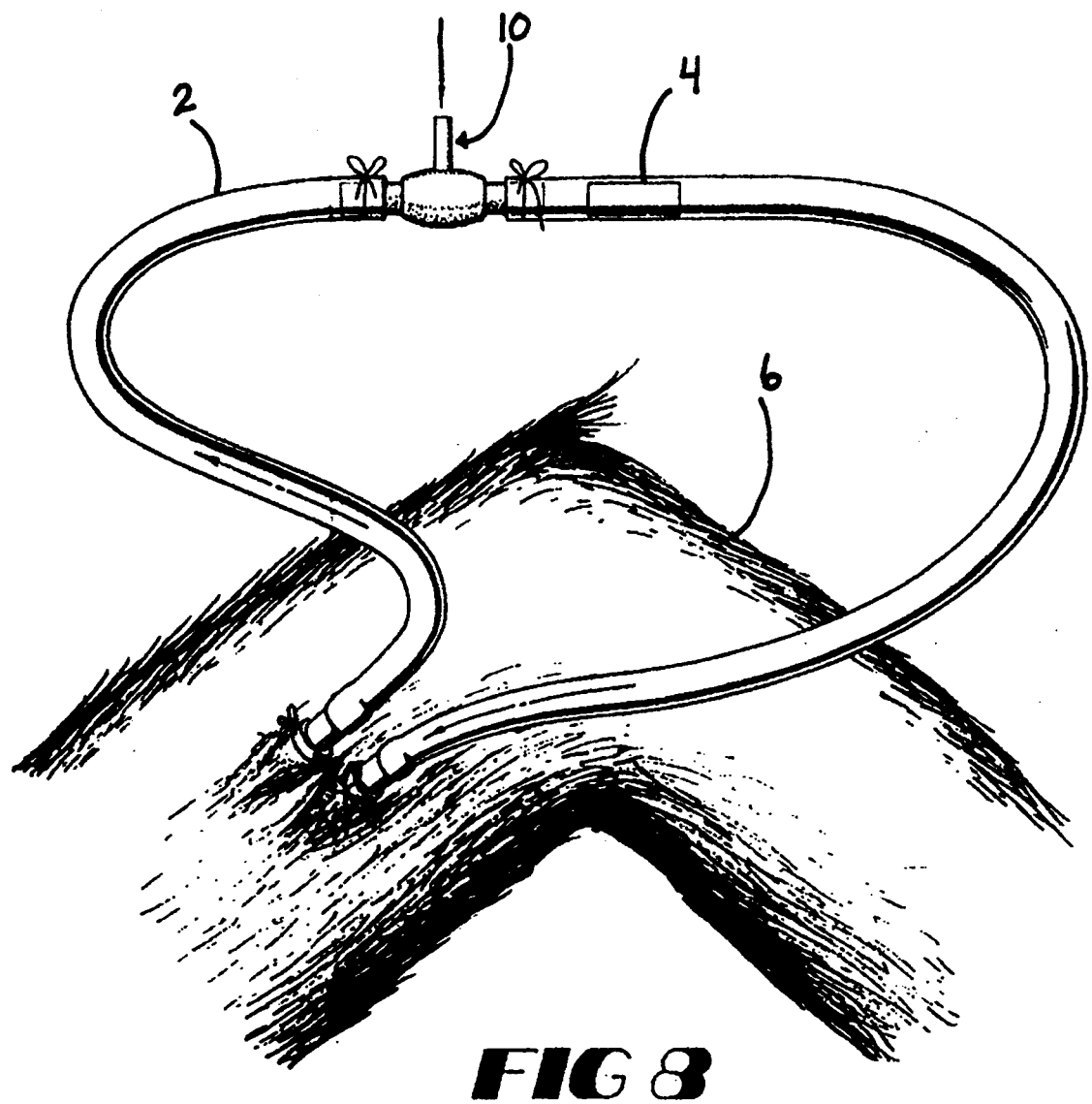
FIG. 8 depicts a perspective view of the first embodiment of the present invention inserted in a baboon femoral arteriovenous shunt.

III. Ex vivo studies with arteriovenous shunts. Referring to FIG. 8, to document the efficiency of this method of local drug delivery, a local drug delivery device 10 of the present invention was inserted several times as an extension segment of baboon femoral arteriovenous shunt 2 and placed 2-3 cm proximal to a segment of highly thrombogenic DACRON ® vascular graft material 4. Blood flow through the infusion device 10 and DACRON ® segment 4 was regulated at 100 ml/min, a value typical of those found in the carotid and iliac arteries of approximately 10 kg baboons 6. This model of DACRON ® graft thrombosis, and its usefulness for assessing the effects of antithrombotic therapy, has been described previously (See, e.g., S. R. Hanson, et al.,*Arteriosclerosis,* 5:595-603, (1985); S. R. Hanson, et al, *J Clin Invest,* 81:149-158, (1988); A. Gruber, et al., *Blood,* 73:639-642, (1989); A. Gruber, et al., *Circulation,* 84:2454-2462, (1991); and W. C. Krupski, et al, *Surgery* 112:433-440, (1992)).

Agents infused include the antithrombins D-Phe-Pro-Arg chloromethyl ketone (PPACK) and hirudin, and an RGD-type peptide inhibitor of platelet glycoprotein IIb/IIIa having the structure: MPr.(hArg).-Gly.Asp.Trp.Pro.Cys-NH$_2$, where hArg is homoarginine, and the peptide is cyclized between mercaptopropionic acid (Mpr) and cysteine as set forth in the Sequence Listing as SEQ ID NO : 1. These agents were chosen since we have previously studied their effects following intravenous infusion in the same thrombosis model, thereby allowing comparison with the local delivery approach. (See, e.g., S. R. Hanson, et al., *Proc Natl Acad Sci USA,* 85:3184-3188, (1988); A. B. Kelly, et al., *Blood,* 77:1006-1012, (1991); and S. R. Hanson, et al., *Thrombosis and Hemostasis,* 65(6):813, (1991)).

All agents were mixed with isotonic saline which was infused at 0.1 ml/min. Total platelet deposition was measured over 30 minutes of blood exposure as determined by [111]Indium-platelet imaging. Dose-response curves for local and intravenous (i.v.) administration were virtually coincident for the three agents. These data imply only that the shape of the i.v. and local infusion dose-response curves for each agent are similar. These data also allow determination of the relative efficiency of i.v. vs. local drug administration. Thus, utilizing the optimization procedures taught herein, the local dose requirement for inhibiting platelet thrombus formation was reduced 720-fold (vs. i.v. therapy) for PPACK, 100-fold for RGD peptide, and 23-fold for hirudin. Similarly, laws of first-order clearance kinetics predict that, when agents are infused by the local route, local boundary layer drug concentrations will exceed systemic circulating levels by the same factors (i.e., by 720-fold for PPACK). This method for predicting dosage requirements can be utilized for other substances to determine an appropriate treatment regimen.

I.V. infusion of PPACK at 45 $\mu$g/kg-min into 10 kg baboons having a plasma volume of ~500 ml blocks thrombus formation and produces steady-state plasma levels of >1 $\mu$g/ml with an apparent in vivo half life of PPACK of about 2.5 minutes (S. R. Hanson, et al, *Proc Natl Acad Sci USA*, 85:3184-3188, (1988)). The theoretical and in vitro studies (in the optimization procedures discussed herein) predict that in the shunt study, infusion of PPACK solution (5 $\mu$g/ml) at a rate of 0.1 ml/min should achieve a wall concentration of 1-2 $\mu$g/ml (i.e., 60-80% dilution of infusate), which is essentially that plasma level previously shown to effectively block thrombus formation in the i.v. infusion studies. These data with PPACK therefore denote that the infused material is effectively concentrated in a boundary layer that occupies only approximately 5% of the cross section of a 4 mm i.d. tube having a total flow of 100 ml/min. Since the boundary layer/systemic drug levels attained with local infusion are also known for the RGD-peptide (ratio=100) and hirudin (ratio=23), our data predicts a half life for RGD-peptide of approximately 17 min, and a half life for hirudin of approximately 60 min, which are in good accord with clinical and experimental animal observations.

In summary, the boundary layer into which effectively all drug is concentrated 2-3 cm downstream comprises an annular ring at the blood-vessel interface occupying only about 5% of the tube cross-sectional area. Thus, total effective drug requirements at that area will be remarkably small. For example, to maintain local PDGF-BB (platelet derived growth factor) levels at 10 ng/ml, we would infuse PDGF solution (100 ng/ml at 0.05 ml/min (i.e., 90% dilution of infusate) or approximately 7/$\mu$g per day, a remarkably small requirement for treatment of larger animals.

Therefore, where standard therapeutic levels are known for a substance administered by conventional i.v. (systemic) therapy, the dosage and treatment regimen for local delivery of the substance utilizing the device of the present invention can be predicted. Further, while the pharmacokinetics of many agents may be complex, these issues are irrelevant for agents having haft lives less than several hours, since drug recirculation will contribute very little to the boundary layer drug levels. These data indicate that the methods of the present invention have the advantage of providing local drug levels in known quantities to good approximation to target tissues.

IV. In vivo studies. We implanted 6 devices, as shown in FIG. 1 and FIG. 2, into the baboon carotid arteries, proximal to sites of balloon catheter angioplasty, with continuous infusion of agents including bFGF (basic fibroblast growth factor) and recombinant hirudin (Ciba-Geigy, Horsham, U.K.), for periods of 12 hours and 3 days. Doses infused were 100 $\mu$g/day (bFGF) and 14 mg/day (hirudin). All arteries were harvested at 3 days; analyses were performed on segments 1-3 cm distal to the infusion site. In all cases, the volume infused was 0.05 ml/min, which was adequate to maintain the blood flow surface of the infusion device free of adherent blood elements (the circumferential uniformity of infused agents is further suggested by the data of Example III since we know that DACRON ® grafts actively thrombose if even a portion of the thrombogenic DACRON ® surface is untreated); See, A. Gruber, et al., *Blood*, 73:639-642, (1989)).

Specimens from animals treated with hirudin (5 animals) and bFGF (1 animal) were evaluated for early SMC proliferation by the cyclin (proliferating cell nuclear antigen) assay (U. Zeymer, et al., *Am J Pathol*, 141:685-690, (1992)). One preliminary study with bFGF showed a striking increase in lumenal SMC proliferation with virtually every cell in the lumenal third of the media of the vessel staining positively. In this study, the local infusion device was interposed into the carotid artery using proximal and distal end-to-end surgical anastomoses.

In the first study with hirudin locally infused (10 $\mu$g/min; 1.5 mg/kg/day) in the same manner, there was continued blood oozing at the distal anastomotic site; hence the infusion was stopped after 12 hours. However, this study indicated that 12-hour hirudin treatment (with vessels harvested 2.5 days later) did not reduce SMC proliferation. For subsequent studies with hirudin, we therefore developed the modified approach shown in FIG. 1 and FIG. 2, whereby the distal end 6 of the local infusion device 10 allowed the injured vessel (conduit) 2 to be cannulated (rather than anastomosed). With this method, there was little bleeding with continuous hirudin therapy, initiated at the time of device placement and balloon injury of the distal vessel. Hirudin therapy was continued over 3 days. This strategy represents a practical solution to the problem of possible local bleeding complications when administration of antihemostatic agents is begun intraoperatively. Data from the first animal continuously treated with hirudin for 3 days in this way showed a striking reduction in cell proliferation (5.5% ±0.7 cyclin positive cells) vs. the contralateral control vessel from the same animal (33.1% ±3.2 cyclin positive cells). We have now confirmed this result in a total of 4 animals. In the 4 control vessels (which were balloon injured in exactly the same manner with proximal placement of a control infusion device), i.e., the carotid arteries from the same animals which were contralateral to the vessels treated by local hirudin therapy, 20.7 ±1.8% of medial SMC were cyclin positive. On the treated side, only 4.3% of SMC (smooth muscle cells) were cyclin positive, a reduction of 80% (p<0,01).

This study also illustrates that local infusion produces low systemic drug levels because control data were obtained with other vessels from the same animal. (in the 4 treated animals APTT clotting times were <45 sec and bleeding times were normal). Further, this study suggests the importance of the thrombin pathway in SMC proliferation and thus provides a strong rationale for therapy with: 1) other antithrombins, 2) antagonists of the thrombin receptor, and 3) agents which may limit thrombin production, e.g., potent platelet antagonists.

Finally, a possible contribution of thrombin to ongoing and late lesion formation is suggested by recent in situ hybridization studies performed on baboon vessels 30 days following carotid artery endarterectomy. At this time point, lumenal SMC comprising the neointimal lesion are still actively proliferating as shown by cyclin (PCNA) staining. Interestingly, these same SMC also show good colocalization for both thrombin receptor and PDGF-A chain mRNAs. Thus, these studies demonstrate that vascular repair in the baboon model may be modulated by both cellular growth factors and factors derived from the hemostatic system.

Although the present process has been described with reference to specific details of certain embodiments thereof, it is not intended that such details should be regarded as limitations upon the scope of the invention except as and to the extent that they are included in the accompanying claims.

What is claimed is:

1. A device for the local delivery of a substance into a natural tissue conduit in the mammalian body, comprising:
   a) a first element comprised of a biocompatible material which can be affixed to the conduit and having a first surface, an opposite second surface, and an intermediate porous portion which communicates the second surface with the first surface, wherein the first surface of the porous portion can be placed in fluid communication with the lumen of the conduit; and
   b) a second element comprised of a substantially non-porous biocompatible material which overlays the second surface of the first element, a reservoir being formed between the first element and the second element, the interior of the reservoir being capable of fluid communication with the conduit via the porous portion such that a substance in the reservoir is delivered into the conduit.

2. The device of claim 1, wherein the first element forms a patch which overlies a portion of the conduit.

3. The device of claim 1, wherein the conduit is a blood vessel and the first element is a vascular patch.

4. The device of claim 1, wherein the first element further comprises an elongated tubular segment having a substantially non-compliant, hollow body portion which is open at both ends wherein the first surface is the luminal surface of the tubular segment, and wherein the tubular segment is capable of being affixed to the natural tissue conduit at both of the ends of the tubular segment.

5. The device of claim 4, wherein the conduit is a blood vessel and the first element is a tubular prosthesis.

6. The device of claim 4, wherein the first element forms a tubular vascular prosthesis with a blood vessel.

7. The device of claim 1, further comprising a tube in communication at its first end with the reservoir and at its second end with a remote source of the substance.

8. The device of claim 7, further comprising a pump connected to the second end of the tube for delivering a substance to the reservoir and for creating pressure within the reservoir which exceeds the intraluminal pressure of the natural tissue conduit.

9. The device of claim 1, wherein the first element comprises material selected from the group consisting of biocompatible polymers, metals and ceramics.

10. The device of claim 9, wherein the polymer is selected from the group consisting of fluoropolymer, polyurethane, and polyester.

11. The device of claim 9, wherein the polymer is selected from the group consisting of polyethylene terephthalate and polytetrafluoroethylene.

12. The device of claim 1, further comprising a coating on a portion of the first surface in contact with the lumen of the conduit which improves the biocompatibility of the first surface.

13. The device of claim 8 wherein the coating is selected from the group consisting of silicone rubber, fluorocarbon, hydrocarbon, and polyurethane based polymers.

14. The device of claim 1, wherein the second element is comprised of material selected from the group consisting of biocompatible polymers, metals and ceramics.

15. The device of claim 14, wherein the polymer is selected from the group consisting of silicone rubber, polyurethane, polyfluorocarbon, polyethylene, polycarbonate and polyvinyl chloride.

16. The device of claim 1, wherein the substance is a drug.

17. The device of claim 1, wherein the substance is an anticoagulant.

18. The device of claim 17, wherein the anticoagulant is selected from the group consisting of heparin, hirudin, hirulog, hirugen, activated and non-activated protein C, antagonists of thrombin, Factor Xa and activated and non-activated coagulation factors.

19. The device of claim 1, wherein the substance antagonizes platelet deposition and thrombus formation.

20. The device of claim 19, wherein the substance is selected from the group consisting of plasmin, tissue plasminogen activator (tPA), urokinase (UK), single chain prourokinase (scuPA), streptokinase, prostaglandins, cyclooxygenase inhibitors, phosphodiesterase inhibitors, thromboxane synthetase inhibitors, antagonists of glycoprotein receptors including (GP) Ib,GP IIb-/IIIa, antagonists of collagen receptors, and antagonists of platelet thrombin receptors.

21. The device of claim 1, wherein the substance affects platelet metabolic function.

22. The device of claim 21, wherein the substance is selected from the group consisting of prostaglandins, cyclooxygenase inhibitors, phosphodiesterase inhibitors, thromboxane inhibitors, inhibitors of calcium transport, and cyclic AMP agonists.

23. The device of claim 1, wherein the substance prevents restenosis of a blood vessel.

24. The device of claim 21, wherein the substance is selected from the group consisting of a growth factor, a growth factor inhibitor, growth factor receptor antagonist, transcriptional repressor, translational repressor, antisense. DNA, antisense RNA, replication inhibitor, inhibitory antibodies, antibodies directed against growth factors, bifunctional molecules comprising a growth factor and a cytotoxin, and bifunctional molecules comprising an antibody and a cytotoxin.

25. The device of claim 1, wherein the substance is a vasodilator.

26. The device of claim 23, wherein the substance is selected from the group consisting of prostaglandins, thromboxane antagonists, nitroglycerin, nitroprusside, agents which liberate nitric oxide, and agents which inhibit calcium transport.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: circular ( i i ) MOLECULE TYPE: peptide ( i x ) FEATURE:
      ( A ) NAME/KEY: Peptide
      ( B ) LOCATION: 1..7
      ( C ) OTHER INFORMATION: /note="RGD-type peptide;
         inhibits platelet glycoprotein IIb/IIIa; Xaa/pos.
         1=mercaptopropiniv acid (Mpr); Xaa/pos.
         2=homoarginine; and the peptide is cyclized between
         mercaptoproprionic acid and cysteine.

( x i ) SEQUENCE DESCRIPTION: SEQ ID NO:1:

Xaa  Xaa  Gly  Asp  Trp  Pro  Cys
   1                   5